United States Patent [19]

Norton

[11] Patent Number: 5,735,609
[45] Date of Patent: Apr. 7, 1998

[54] CONTAINER FOR HOLDING STERILIZED ELEMENTS

[75] Inventor: Paul H. Norton, Trumbauersville, Pa.

[73] Assignee: The West Company, Lionville, Pa.

[21] Appl. No.: 682,032

[22] Filed: Jul. 16, 1996

[51] Int. Cl.⁶ .................................................. B65D 33/16
[52] U.S. Cl. .................. 383/33; 53/434; 422/294; 383/37; 383/41; 383/93; 493/212
[58] Field of Search ............... 53/434; 422/294; 493/212, 213; 383/33, 37, 41, 80, 93

[56] References Cited

U.S. PATENT DOCUMENTS

| | | | |
|---|---|---|---|
| 2,173,288 | 9/1939 | Shapiro | 383/80 |
| 2,572,669 | 10/1951 | Sarge et al. | |
| 3,016,284 | 1/1962 | Trexler | |
| 3,069,734 | 12/1962 | Leuthner | |
| 3,554,688 | 1/1971 | Cassidy | |
| 3,647,386 | 3/1972 | Gilford | 383/93 |
| 3,656,668 | 4/1972 | Liebertz | 383/80 |
| 3,716,961 | 2/1973 | Cope et al. | |
| 4,081,942 | 4/1978 | Johnson | |
| 4,099,914 | 7/1978 | Gustafsson et al. | |
| 4,109,441 | 8/1978 | Shaw | |
| 4,419,376 | 12/1983 | Hersom et al. | |
| 4,603,538 | 8/1986 | Shave | |
| 4,636,391 | 1/1987 | Pike | |
| 4,696,840 | 9/1987 | McCullough et al. | 383/80 |
| 4,714,595 | 12/1987 | Anthony et al. | |
| 4,805,378 | 2/1989 | Anderson | |
| 4,885,897 | 12/1989 | Gryouda et al. | |
| 4,974,393 | 12/1990 | Rich et al. | 53/434 |
| 4,991,633 | 2/1991 | Wong | |
| 5,014,494 | 5/1991 | George | |
| 5,171,523 | 12/1992 | Williams | |
| 5,346,312 | 9/1994 | Mabry et al. | |
| 5,447,699 | 9/1995 | Papciak et al. | |
| 5,501,525 | 3/1996 | Cox et al. | 53/434 |
| 5,636,871 | 6/1997 | Field | 383/33 |

*Primary Examiner*—Stephen P. Garbe
*Attorney, Agent, or Firm*—Panitch Schwarze Jacobs & Nadel, P.C.

[57] ABSTRACT

A container for holding elements to be sterilized prior to introduction into an isolation system having an isolated inner region. The container includes a flexible bag having a first end defining a first opening for removing the elements from the flexible bag. A transfer port is attached to the flexible bag proximate the first end. The transfer port is engageable with the isolation system for transferring the sterilized elements into the isolation system. The transfer port has an exterior surface, and a bore extends through the transfer port and the exterior surface. The exterior surface has a clamp receiving area and a groove located in proximity to a first end of the bore. The first end of the flexible bag is located in the groove. A clamp is located around the flexible bag proximate to the first end. A portion of the flexible bag is located between the clamp and the clamp receiving area on the transfer port to clamp the flexible bag to the transfer port. A sealing material is located in the groove and encapsulates the first end of the flexible bag to hermetically seal the flexible bag to the transfer port.

7 Claims, 1 Drawing Sheet

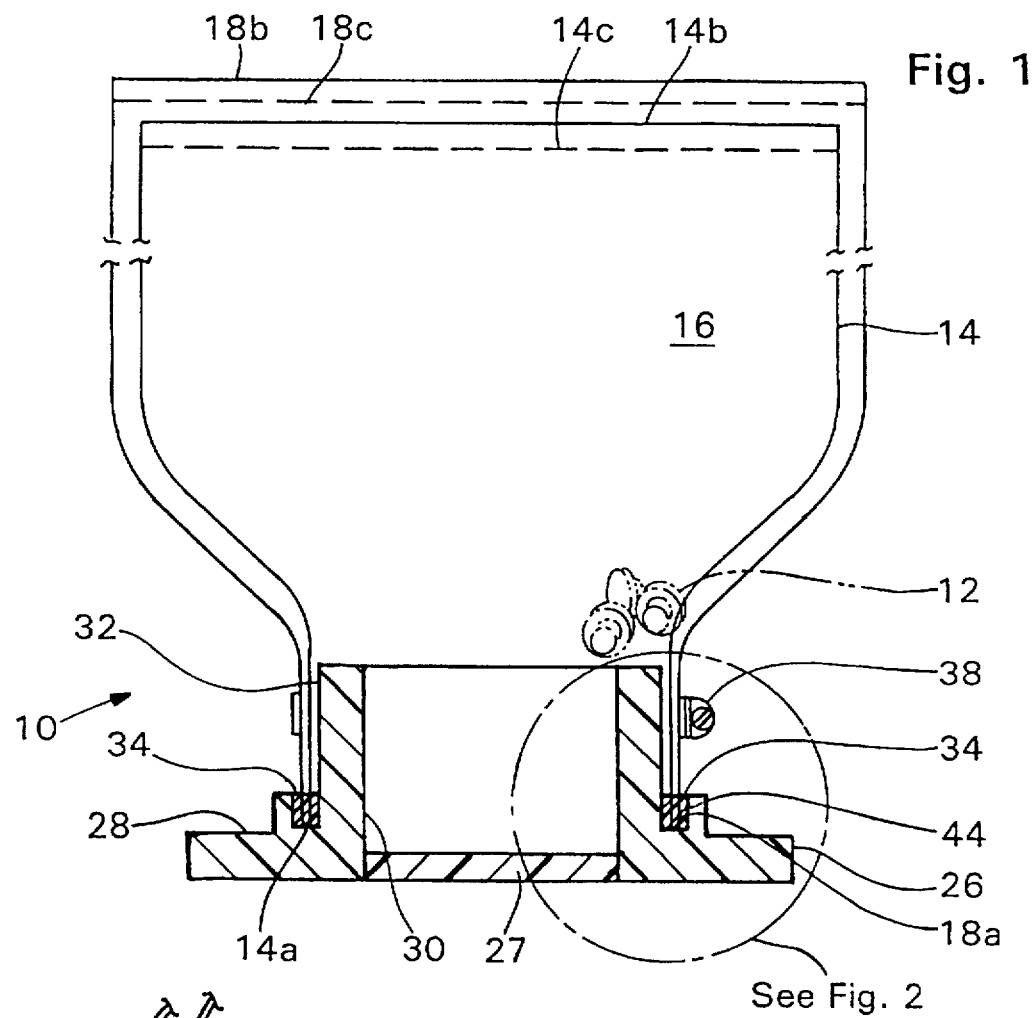
Fig. 1
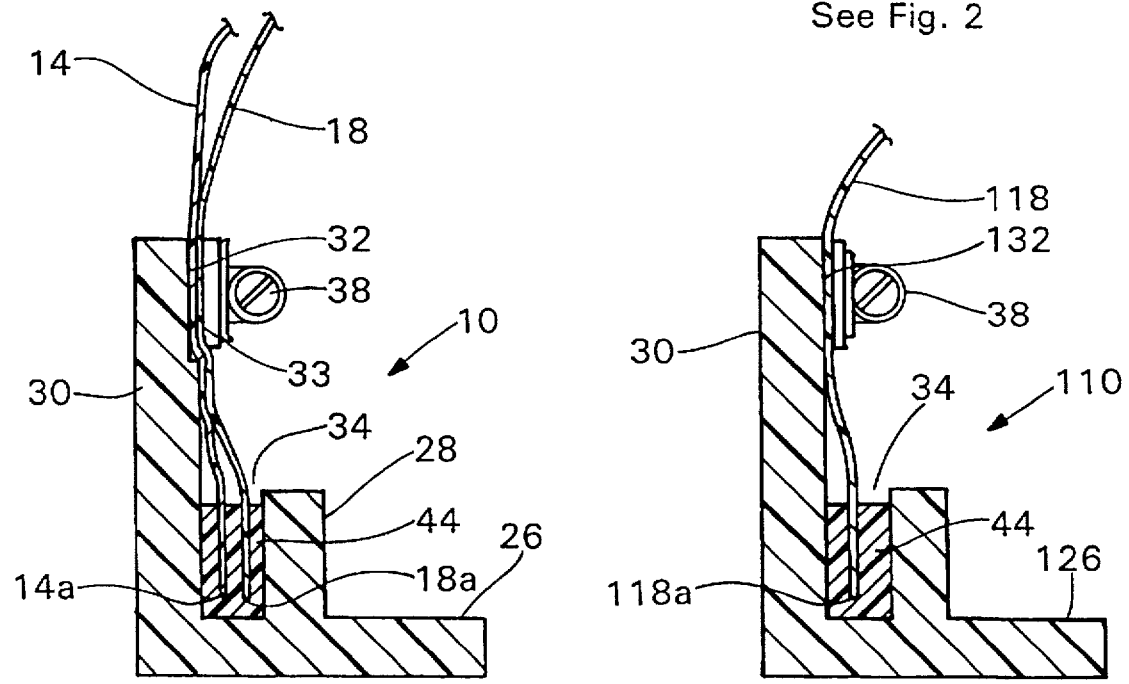
Fig. 2
Fig. 3

CONTAINER FOR HOLDING STERILIZED ELEMENTS

FIELD OF THE INVENTION

The present invention relates to a container for holding sterilized elements and, more particularly, to a container having a transfer port for transferring the sterilized elements into an isolation system or other sterile area.

BACKGROUND OF THE INVENTION

In the past, packaging of sterile products was carried out in clean rooms which were maintained in an isolated, sterile environment. Personnel working in such clean rooms generally had to be entirely covered in protective clothing to prevent contamination of the equipment or products being packaged.

In order to avoid the expense of operating and maintaining clean room environments, barrier-isolated equipment has been introduced which maintains a local sterile environment directly around the equipment which can be accessed through glove portals or by other means. This eliminates the requirement for a clean room and results in savings in capital costs, as well as reduction of losses due to contamination.

There is a requirement for introducing parts or other material into such isolated systems without jeopardizing the sterility of the parts or the atmosphere within the isolated system. One method for solving this problem involves providing a cleaning and sterilizing machine next to the isolation system. The machine includes a treatment vessel which receives the articles to be sterilized, such as closure elements for pharmaceutical containers. The closure elements are sterilized within the treatment vessel and are then passed into the isolation system. Prior to passing the closure elements from the treatment vessel to the isolation system, the conduit between the treatment vessel and the isolation system is sterilized.

However, positioning a cleaning and sterilizing machine proximate to an isolation system, as described above, requires the processing and packaging company to incur additional cost for the cleaning and sterilizing machine, as well as requiring additional room for the cleaning and sterilizing equipment adjacent to each isolation system.

Another solution to this problem, which is described in U.S. Pat. No. 5,447,699, which was jointly invented by the present inventor and is assigned to the assignee of the present invention, provides a combination container for holding sterilized elements, such as vial stoppers, and a sterilizable transfer port for transferring the sterilized elements located on the isolation system. The container is formed of a flexible bag which receives the sterilized elements and a collar having a sealed closure which can be sterilized when it is connected to the isolation system to transfer the elements from the container to the isolation system. This allows the required sterilized elements to be sterilized at a different location prior to shipping to the processing and packaging company where the sterilized elements are fed in to the isolation system, such as a system for bottling pharmaceuticals.

One problem with the known containers for holding and storing sterilized elements is the connection between the collar or transfer port component of the container for holding the sterilized elements and the flexible bag component. In order to assure that the sterilized elements within the bag remain in their sterile condition, the connection between the flexible bag and the rigid transfer port or collar must be hermetically sealed to prevent ingress of bacteria, moisture or other contaminants. If the seal between the flexible bag component and the transfer port component is not hermetically sealed, then the entire container of sterilized elements cannot be used and must either be scrapped or shipped back to the provider for reprocessing and sterilizing.

SUMMARY OF THE INVENTION

Briefly stated, the present invention comprises a container for holding elements to be sterilized prior to introduction into an isolation system having an isolated inner region. The container includes a first flexible bag defining a cavity for containing the elements. The flexible bag includes a first end defining a first opening for removing the elements from the flexible bag. A transfer port is attached to the first end of the flexible bag. The transfer port is engageable with the isolation system for transferring the sterilized elements into the isolation system. The transfer port has an exterior surface which includes a clamp receiving area, and a bore extends through the transfer port and exterior surface. A groove is located in proximity to a first end of the bore. The first end of the first flexible bag is located in the groove. A clamp is located around the flexible bag proximate to the first end. A portion of the flexible bag is located between the clamp and the clamp receiving area on the transfer port to clamp the flexible bag to the transfer port. A sealing material is located in the groove and encapsulates the first end of the first flexible bag to hermetically seal the first flexible bag to the transfer port.

In another embodiment, the present invention provides a method of producing a containing for holding sterilized elements, with the container including a transfer port for connection to an isolation system. The method comprises the steps of:

providing a flexible bag having a first end defining a first opening;

encapsulating the first end of the flexible bag in a groove in a transfer port which is engageable with the isolation systems;

clamping a portion of the flexible bag proximate to the first end of the flexible bag to the transfer port.

BRIEF DESCRIPTION OF THE DRAWING

The foregoing summary, as well as the following detailed description of preferred embodiments of the invention, will be better understood when read in conjunction with the appended drawing. For the purpose of illustrating the invention, there is shown in the drawing embodiments which are presently preferred. It should be understood, however, that the invention is not limited to the precise arrangements and instrumentalities shown. In the drawing:

FIG. 1 is a cross-sectional view of a container in accordance with the present invention;

FIG. 2 is an enlarged fragmentary view of a portion of FIG. 1; and

FIG. 3 is an enlarged fragmentary view of a second embodiment of the invention similar to FIG. 2.

DETAILED DESCRIPTION OF PREFERRED EMBODIMENTS

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the container for holding sterilized elements and designated parts thereof. The terminology includes the words above specifically mentioned, derivatives thereof and words of similar import.

Referring to the drawing, wherein like numerals indicate like elements throughout, there is shown in FIGS. 1 and 2 a first preferred embodiment of a container 10 for holding elements 12 (only a representative sample being shown), which are to be sterilized prior to introduction into an isolation system (not shown) having an isolated inner region. Isolation systems are well known to those of ordinary skill in the art, and therefore, further description is omitted for purposes of convenience only, and is not considered limiting. One system which utilizes a container comprising a flexible bag affixed to a collar or transfer port which can be connected to a port on an isolation system is described in U.S. Pat. No. 5,447,699, which is incorporated herein by reference as if fully set forth.

Referring now to FIGS. 1 and 2, the container 10 of the present invention comprises a flexible bag 14 which defines a cavity 16 for containing the elements 12. The flexible bag 14 includes a first end 14a which defines a first opening for removing the sterilized elements from the first flexible bag 14, and a second end 14b which defines a second opening for placing the elements 12 to be sterilized in the first flexible bag 14.

In the first preferred embodiment, there are two flexible bags 14, 18. The first flexible bag 14 is located inside the second flexible bag 18, and each flexible bag 14, 18 has first and second ends 14a, 18a, 14b, 18b, respectively, with the first ends 14a, 18a defining first openings and the second ends 14b, 18b defining second openings.

In the first preferred embodiment, the first flexible bag 14 is preferably made of a permeable material, such as TYVEK®, which allows steam to pass through the first bag 14 and sterilize the elements 12 located therein. Preferably, the second end 14b of the first flexible bag 14 is sealed along a seal line 14c after the elements 12 are located therein. Those skilled in the art will recognize from the present disclosure that the first flexible bag 14 could be made of other suitable permeable or impermeable materials, if desired, depending upon the particular application.

In the first preferred embodiment, the second flexible bag 18 is made of an impermeable material such as plastic or a multi-layer polymeric material, which protects the elements 12 inside the first bag 14 from contamination after they have been sterilized. The open second end 18b of the second bag 18 is sealed along a seal line 18c. It will be recognized by those skilled in the art from the present disclosure that the shape and size of the first and second flexible bags 14, 18 can be varied as desired, depending on the quantity of sterilized elements that are required.

Still with reference to FIGS. 1 and 2, a rapid transfer port or collar 26 is attached to the first end 14a of the first flexible bag 14. The transfer port includes a sealable door 27, and is engageable with the isolation system (not shown) for transferring sterilized elements 12 into the isolation system. The transfer port 26 has an exterior surface 28 and a bore 30 extending therethrough. The exterior surface 28 has a clamp receiving area 32 with a recess 33. A groove 34 is located in proximity to the bore 30 and extends around the bore 30. The first end 14a of the first flexible bag 14 is located in the groove 34 such that the opening defined by the first end 14a is in registry with the bore 30. In the first preferred embodiment 10, the first ends 14a, 18a of the first and second flexible bags 14, 18 are located in the groove 34 such that the openings defined by the first ends 14a, 18a are in registry with the bore 30.

Those skilled in the art will recognize that various transfer port configurations could be used in conjunction with the present invention, and that the sealing of the bore 30 in the transfer port 26 could be accomplished by various other means, such as a removable seal, and the specific configuration of the transfer port 26 and the transfer port seal can be varied within the scope of the present invention. It is preferred that the transfer port 26 be constructed of a high strength material capable of withstanding repeated sterilization procedures, such as a suitable polymeric or metallic material.

Still with reference to FIGS. 1 and 2, a clamp 38 is located around the flexible bag 14 proximate to the first end 14a. A portion of the flexible bag 14 is located between the clamp 38 and the recess 33 in the clamp receiving area 32 on the transfer port 26 to clamp the flexible bag 14 to the transfer port 26. Preferably, portions of the first and second flexible bags 14, 18 are located between the clamp 38 and the recess 33 to clamp the flexible bags 14, 18 to the transfer port 26. It will be recognized by those skilled in the art from the present disclosure that the clamp receiving area 32 of the transfer port 26 need not include a recess 33.

In the preferred embodiment, the clamp 38 is a band clamp of the type generally known to those of ordinary skill in the art. However, it will be recognized by those skilled in the art from the present disclosure that any type of clamp or strap may be used to secure the first and second flexible bags 14, 18 to the transfer port 26 and provide a connection between the transfer port 26 and the first and second flexible bags 14, 18 to assist in holding the bags 14, 18 in position as sealing material 44 is placed in the groove 34, as described in detail below. The clamp also prevents the elements 12 from collecting or jamming around the connection between the transfer port 26 and the bags 14, 18.

A sealing material 44 is located in the groove 34 to encapsulate the first end 14a of the flexible bag 14 to hermetically seal the first end 14a of the flexible bag 14 to the transfer port 26. Preferably, the first ends 14a, 18a of both flexible bags 14, 18 are encapsulated in the sealing material 44 in the groove 34. In the preferred embodiment, the sealing material 44 is a hardenable liquid resin which is placed into the groove 34 and allowed to solidify around the first ends 14a, 18a of the flexible bags 14, 18. Preferably, the sealing material is a two-part epoxy. However, it will be recognized by those skilled in the art from the present disclosure that other types of adhesive systems or sealants may be used.

Referring now to FIG. 3, a second preferred embodiment of a container 110, is shown. The second preferred embodiment of the container 110 for holding elements 12 is similar to the first embodiment 10, and like elements have been identified with the same or like reference numerals.

As shown in FIG. 3, the container 110 includes only a single flexible bag 118 which is attached to the transfer port 126 by the clamp 38 located around the flexible bag 118 proximate to the first end 118a, and a portion of the flexible bag 118 is located between the clamp 38 and the clamp receiving area 132. In the second preferred embodiment, the clamp receiving area 132 is smooth, and does not include the recess 33 as in the first embodiment 10. Preferably, the flexible bag 118 is made of a non-permeable material to protect the sterilized elements 12 in the bag. The first end 118a of the flexible bag 118 is located in the groove 34, and sealing material 44 is used to encapsulate the first end 118a of the flexible bag 118 to hermetically seal the flexible bag 118 to the transfer port 126.

It will be recognized by those skilled in the art from the present disclosure that more than two flexible bags can be used for particular applications, if desired, and that the first ends of the two or more bags can be encapsulated in a single groove 34, as described above, or in separate, spaced apart grooves on the transfer port, if desired.

A method of producing the containers 10, 110 of the present invention is also described below. One or more flexible bags 14, 18, 118 having first ends 14a, 18a, 118a defining respective openings are provided. The first end(s) 14a, 18a, 118a is(are) located in the groove 34 in the transfer port 26, 126 which is engageable with the isolation system. The first end(s) 14a, 18a, 118a of the flexible bag(s) 14, 18, 118 is(are) encapsulated with a sealing material 44 in the groove 34 on the transfer port 26. A portion of the flexible bag(s) 14, 18, 118 proximate to the first end(s) 14a, 18a, 118a is(are) clamped to the transfer port 26, 126 to provide a load carrying attachment of the flexible bag(s) 14, 18, 118 to the transfer port 126.

This process ensures a hermetic seal being formed between the flexible bags 14, 18, 118 and transfer port 26, 126 which eliminates the possibility of contamination of sterilized elements 12 located in the flexible bags 14, 18, 118 through the interface between the flexible bags 14, 18 and the transfer ports 26, 126.

The container 10 was subjected to testing which included injection of a liquid dye into a sealed container 10 in accordance with the present invention. The assembly was manipulated such that the dye came in full contact with the connection area between the flexible bags 14, 18 and the transfer port 26. A container would pass the test when no dye could be found outside of the container after subjecting the bag to various conditions. Containers having a simple heat seal between the bag and the transfer port or a mechanical connection eventually leaked, and were found to be unsuitable for use in connection with isolation systems.

In use, the container 10 in accordance with the first preferred embodiment is produced in accordance with the above-described method, and is used for in situ sterilization of elements 12 after they have been packaged in the first flexible bag 14. The second ends 14b, 18b of the first and second bags 14, 18 are left open, and the transfer port 26 is provided in a sealed condition, with the door 27 being hermetically sealed in a closed position. The elements 12 to be sterilized, such as vial stoppers, are placed inside the first permeable bag 14 through the opening at the second end 14b. The second end 14b is then sealed along seal line 14c. Alternatively, the flexible bags 14, 18 could have only the first end 14a open. The elements 12 would then be placed through and removed from the opening defined by the first end 14a, and the elements can be placed in the first end 14a of the first flexible bag 14 through the transfer port 26 prior to closing and sealing the transfer port 26. The container 10, which contains the elements 12 to be sterilized, is then moved to an area for sterilization. Sterilization can be accomplished in an autoclave by passing steam through the first permeable bag 14 to sterilize the elements 12 within the bag. The autoclave is then evacuated by a vacuum force, and the opening defined by the second end 18b of the second non-permeable bag 18 is sealed by heat sealing or other means to provide a hermetic seal 18c along the second end 18b. The container 10 with the sterilized elements 12 can then be stored until the elements 12 are needed.

When the elements 12 are required, the transfer port 26 is attached to a port (not shown) on an isolation system, and after sterilizing the connection area between the transfer port 26 on the container 10 and the port on the isolation system, the elements 12 can be transferred into the isolation system.

Other types of sterilization procedures may be used, such as gamma irradiation. When gamma irradiation is used for sterilization, preferably the container 110 with a single non-permeable bag 18 is used to hold the elements 12. Alternatively, elements 12 which are sterilized prior to packaging can placed in the container 110 in a sterile environment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A container for holding elements which are to be sterilized prior to introduction into an isolation system having an isolated inner region, the container comprising:

a first flexible bag defining a cavity for containing the elements, the flexible bag including a first end defining a first opening for removing the elements from the flexible bag;

a transfer port being engageable with the isolation system for transferring elements into the isolation system, the transfer port having an exterior surface which includes a clamp receiving area, and a bore extends through the transfer port and the exterior surface, a groove being located on the transfer port proximate the bore and which extends around the bore, the first end of the first flexible bag being located in the groove such that the first opening is in registry with the bore;

a clamp located around the flexible bag proximate the first end, a portion of the flexible bag being located between the clamp and the clamp receiving area on the transfer port to clamp the flexible bag to the transfer port; and sealing material located in the groove to encapsulate the first end of the flexible bag to hermetically seal the flexible bag to the transfer port.

2. The container of claim 1 further including a second flexible bag having a first end defining a first opening of the second bag, the first flexible bag being located inside the second flexible bag, the first ends of the first and second flexible bags being encapsulated in the sealing material in the groove such that the first openings of the first and second bags are in registry with the bore.

3. The container of claim 2 wherein the first flexible bag is vapor permeable and the second bag is impermeable.

4. The container of claim 2 wherein the first and second flexible bags include second ends defining second openings for placing the elements in the cavity, the opening defined by the second end of the first flexible bag being sealed after the elements are placed in the cavity.

5. The container of claim 1 wherein the first flexible bag includes a second end defining a second opening for placing the elements in the cavity, the opening defined by the second end of the first flexible bag being sealed after the elements are placed in the cavity.

6. The container of claim 1 wherein the sealing material comprises a hardenable liquid resin.

7. A method of producing a container for holding sterilized elements, the container including a transfer port for connection to an isolation system, comprising the steps of:

providing a flexible bag having a first end defining a first opening;

encapsulating the first end of the flexible bag with a sealing material in a groove in a transfer port which is engageable with the isolation system; and clamping a portion of the flexible bag proximate to the first end to the transfer port.

* * * * *